United States Patent
Shin et al.

(10) Patent No.: US 7,801,334 B2
(45) Date of Patent: Sep. 21, 2010

(54) FINGERPRINT RECOGNITION APPARATUS INCLUDING STERILIZING FUNCTION AND METHOD FOR STERILIZING THE SAME

(75) Inventors: Yo-Shik Shin, Seoul (KR); Geum-yong Kim, Seoul (KR)

(73) Assignee: Union Community Co., Ltd., Seoul (KR)

( * ) Notice: Subject to any disclaimer, the term of this patent is extended or adjusted under 35 U.S.C. 154(b) by 853 days.

(21) Appl. No.: 11/723,640

(22) Filed: Mar. 21, 2007

(65) Prior Publication Data
US 2008/0187190 A1 Aug. 7, 2008

(30) Foreign Application Priority Data
Feb. 5, 2007 (KR) .................... 10-2007-0011571

(51) Int. Cl.
G06K 9/00 (2006.01)
G06K 7/00 (2006.01)
G06T 1/00 (2006.01)
G01L 1/24 (2006.01)

(52) U.S. Cl. ................. 382/115; 382/127; 382/312; 340/5.83; 73/862.624

(58) Field of Classification Search ............ 382/124, 382/126, 115, 125, 127, 118, 312, 272, 116, 382/275, 266, 232, 100; 345/173, 156; 340/5.53, 340/5.83, 5.8, 5.52, 5.81; 356/71; 73/862.624, 73/862.381, 862.621; 713/186; 257/414, 257/E27.111, E27.133, E27.147, E29.282; 902/1, 3
See application file for complete search history.

(56) References Cited

U.S. PATENT DOCUMENTS

| | | | | |
|---|---|---|---|---|
| 5,737,439 | A * | 4/1998 | Lapsley et al. | 382/115 |
| 6,330,345 | B1 * | 12/2001 | Russo et al. | 382/115 |
| 6,813,010 | B2 * | 11/2004 | Kono et al. | 356/71 |
| 6,870,946 | B1 * | 3/2005 | Teng et al. | 382/124 |
| 6,885,017 | B2 * | 4/2005 | Lee et al. | 250/556 |
| 6,927,844 | B2 * | 8/2005 | Higuchi et al. | 356/71 |
| 7,113,621 | B2 * | 9/2006 | Hosokawa | 382/124 |
| 7,123,755 | B2 * | 10/2006 | Shigeta | 382/124 |
| 7,164,782 | B2 * | 1/2007 | Baharav et al. | 382/124 |
| 7,245,745 | B2 * | 7/2007 | Nagasaka et al. | 382/115 |
| 2003/0016345 | A1 * | 1/2003 | Nagasaka et al. | 356/71 |

FOREIGN PATENT DOCUMENTS

JP 10-105691 4/1998

* cited by examiner

*Primary Examiner*—Sheela C Chawan
(74) *Attorney, Agent, or Firm*—Sughrue Mion, PLLC

(57) ABSTRACT

Provided are a fingerprint recognition apparatus including a sterilizing function and a method for sterilizing the same. The fingerprint recognition apparatus includes a sterilizing light source irradiating a sterilizing light on a fingerprint contact surface of a fingerprint sensor to sterilize at all times the fingerprint contact surface which many and unspecified users contact their fingers on repeatedly. Accordingly, it is possible to prevent a route of bacterial infection and improve hygienic conditions.

7 Claims, 5 Drawing Sheets

FINGERPRINT RECOGNITION APPARATUS INCLUDING STERILIZING FUNCTION AND METHOD FOR STERILIZING THE SAME

BACKGROUND OF THE INVENTION

1. Field of the Invention

The present invention relates to a fingerprint recognition apparatus, and more particularly, to a fingerprint recognition apparatus including a function of sterilizing a fingerprint contact surface.

2. Description of the Related Art

Recently, a demand for accuracy of personal authentication increases with the spread of information exchanges through Internet. Applications of a biometric authentication also increase to satisfy such a demand.

In general, the biometric authentication uses fingerprints, eye retinas, irises, voices, facial patterns, electronic signatures and the like. Particularly, a fingerprint recognition method accounts above 70% of the overall biometric authentication market because it has the following advantages: 1) it is harmless because it requires only a contact of a user's finger; 2) it is convenient; and 3) an apparatus for the fingerprint recognition is inexpensive because of its simple structure.

Accordingly, such a fingerprint recognition method is practically implemented to a lap-top computer, a mobile phone, and a personal digital assistant (PDA) as well as an access management and a network security system related to a data security and an electronic commerce.

The above-described fingerprint recognition apparatus is classified into an optical type fingerprint recognition apparatus using an optical lens such as a prism and a hologram, and a non-optical type fingerprint recognition apparatus using a semiconductor device such as a complementary metal oxide semiconductor (CMOS). In general, the fingerprint recognition apparatus adopts a contact type fingerprint recognition that a user touches his or her finger directly on a fingerprint contact surface.

Accordingly, the related art fingerprint recognition apparatus is unhygienic because the fingerprint contact surface, which many and unspecified persons contact their fingers on repeatedly, provides a bacterial infection site all times, which exposes users to a bacterial infection.

SUMMARY OF THE INVENTION

Accordingly, the present invention is directed to a fingerprint recognition apparatus including a sterilizing function and a method for sterilizing the same that substantially obviate one or more problems due to limitations and disadvantages of the related art.

Embodiments of the present invention provide a fingerprint recognition apparatus including a function of sterilizing a fingerprint contact surface thereof and a method for sterilizing the fingerprint contact surface to improve hygienic conditions.

In one aspect of the present invention, there is provided a fingerprint recognition apparatus including a sterilizing function, the apparatus including: a fingerprint sensor unit for obtaining a fingerprint image from a fingerprint that contacts a fingerprint contact surface; a control unit for performing a fingerprint recognition process on the basis of the fingerprint image obtained by the image sensor; and a sterilizing light source for irradiating sterilizing light onto the fingerprint contact surface.

Preferably, the fingerprint recognition apparatus further includes: a sensor unit disposed around the fingerprint contact surface to detect an exposure state of the fingerprint contact surface; and a sterilizing light source controller for controlling the sterilizing light source such that the sterilizing light source is selectively turned on/off depending on an information detected by the sensor unit The sterilizing light source may be disposed at a variety of positions to irradiate sterilizing light on the fingerprint contact surface. For example, when the fingerprint recognition apparatus includes an internal light source that irradiates light for obtaining a fingerprint image onto a rear side of the fingerprint contact surface, the sterilizing light source may be disposed around the internal light source to irradiate the sterilizing light on the rear side of the fingerprint contact surface.

In another aspect of the present invention, there is provided a method for sterilizing a fingerprint contact surface of a fingerprint recognition apparatus, the method comprising: detecting an access of a user's finger to the fingerprint contact surface by using a sensor unit; turning on a sterilizing light source to irradiate sterilizing light on the fingerprint contact surface for a predetermined duration when it is determined, depending on an information detected by the sensor unit, that the user's finger is detached from the fingerprint contact surface after contacting the fingerprint contact surface; and turning off the sterilizing light source when it is determined, depending on an information detected by the sensor unit, that a user's finger accesses the fingerprint contact surface before the predetermined duration has passed since the sterilizing light source was turned on.

Preferably, the method further includes outputting a guide message requesting that the user discontinue contacting the fingerprint contact surface when a predetermined number of operating cycles of the detecting, the turning on and the turning off are performed in succession.

By doing this, the control unit may allow the user to stop contacting the fingerprint contact surface and force the sterilizing operation for the predetermined duration.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiments of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1:
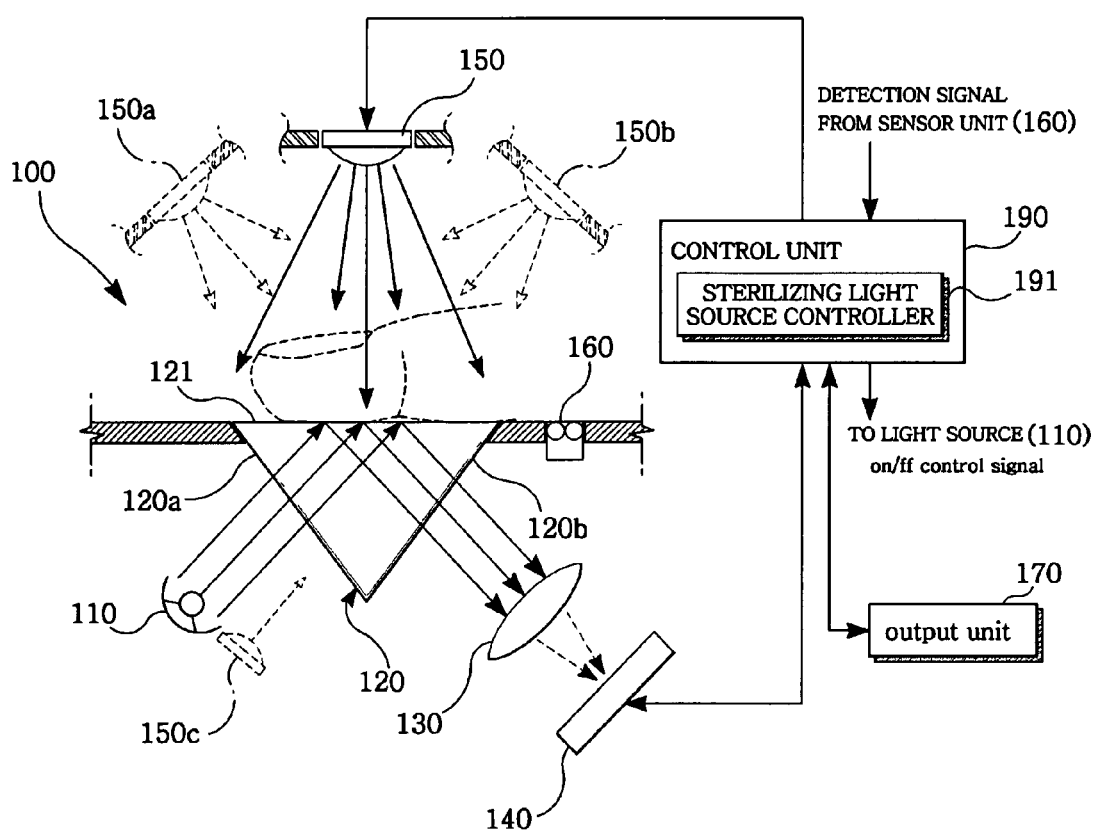
FIG. 1 is a schematic view illustrating main components of an optical type fingerprint recognition apparatus according to an embodiment of the present invention.

Referring to FIG. 1, an optical type fingerprint recognition apparatus 100 according to an embodiment of the present invention includes a light source 110 emitting light to obtain a fingerprint image, a prism 120 with a fingerprint contact surface 121, an optical lens 130 to form the fingerprint image on an image sensor 140, a sterilizing light source 150 irradiating sterilizing light onto the fingerprint contact surface 121, a sensor unit 160 detecting a user's access, an output unit 170, and a control unit 190. The light source 110, the prism 120, the optical lens 130 and the image sensor 140 form a fingerprint sensor unit to obtain the fingerprint image from a user's finger.

Though only an absorption type fingerprint recognition apparatus is illustrated in FIG. 1, the present invention can also be applied to a scattering type fingerprint recognition apparatus. In addition, the prism 120 and the light source 110 can also be varied in shape.

A basic fingerprint recognition process of the optical type fingerprint recognition apparatus will now be described with reference to FIG. 1. When a user touches his or her finger on the fingerprint contact surface 121, the control unit 190 transmits a predetermined control signal to the light source 110 so that the light source 110 emits light to obtain a fingerprint image. The light emitted from the light source 110 passes through an incident surface 120a, the fingerprint contact surface 121 and an emission surface 120b, forms an image on the optical lens 130, and then is received in the image sensor 140. During the above process, light emitted from the light source 110 is absorbed or totally reflected by ridges and valleys of a fingerprint which contacts a fingerprint contact surface 121, and then received in the image sensor 140.

The image sensor 140 transmits to the control unit 190 a digital fingerprint image signal, which is an electric signal corresponding to the light, received in the image sensor 140. The control unit 190 recognizes the user's fingerprint according to an image processing algorithm and an authentication algorithm.

According to an embodiment of the present invention, the sensor unit 160 is provided around the fingerprint contact surface 121 to detect an exposure state, i.e., to detect whether there is a user's finger contacting the fingerprint contact surface 121.

The sterilizing light source 150 is turned on and off selectively by control unit 190 of which the control depends on a detecting signal from the sensor unit 160.—

The sterilizing light source 150 includes a light emitting device having a sterilizing function. The light emitting device having a sterilizing function includes an infrared light emitting device that emits infrared ray of a wavelength of 0.75 μm~1 mm and an ultraviolet light emitting device that emits ultraviolet ray of a wavelength of 100 nm~400 nm.

A variety of light sources such as a point light source including a light emitting diode (LED), a linear or array type light source, and a planar light source can be used as the sterilizing light source 150.

When a housing is formed over the fingerprint contact surface 121, at least one sterilizing light source 150 may be disposed right over the fingerprint contact surface 121 in order to irradiate sterilizing light directly onto the fingerprint contact surface 121.

According to another aspect of the invention, the sterilizing light source, like a sterilizing light source 150a or 150b, may also be disposed around the fingerprint contact surface 121 to irradiate sterilizing light on the fingerprint contact surface 121 at a predetermined angle. In this case, it is also possible to dispose a plurality of sterilizing light sources 150a and 150b such that their optical axes cross each other at a predetermined angle. When the optical axes cross each other at a predetermined angle as described above, the irradiation range of the sterilizing light may be enlarged and even gaps around the fingerprint contact surface 121 in the equipment can be irradiated to improve further the sterilization effect.

According to another aspect of the invention, the position of the sterilizing light source 150 is not limited to a specific position. For example, like a sterilizing light source 150c, the sterilizing light source may be a built-in type, in other words, it may be disposed below the prism 120, such as near the prism 120, the light source 110 or the optical lens 130 to irradiate sterilizing light onto the rear side of the fingerprint contact surface 121.

Also, the sterilizing light source 150 may be disposed at a lateral side of the fingerprint contact surface 121 to irradiate sterilizing light onto the fingerprint contact surface 121 at a sloping angle. Particularly, this can be applied to an equipment that does not have, over the fingerprint contact surface 121, a housing where the sterilizing light source 150 can be placed.

The sensor unit 160 may be a photo-sensor having a light emitting part and a light receiving part, for example. The sensor unit 160 may be disposed around the fingerprint contact surface 121 to detect whether a user's finger or other objects approaches or covers the fingerprint contact surface 121. The sensor unit 160 outputs a detection signal regarding the detection information to the control unit 190.

The output unit 170 may provide a predetermined guide message to a user in response to a control signal of the control unit 190. The output unit 170 may include an audio output device or a display device that output the guide message in the form of an audio signal or an image signal, respectively. The guide message may include a message requesting a user to stop touching the fingerprint contact surface while the sterilizing operation is performed, for example.

The control unit 190 controls operations of the fingerprint recognition apparatus 200 on the whole. The control unit 190 includes a sterilizing light source controller 191 for performing a sterilizing function.

The sterilizing light source controller 191 controls the sterilizing light source 150 such that it is turned on and off on the basis of a detection signal received from the sensor unit 160, so that the sterilizing operation is not performed while a user's finger contacts the fingerprint contact surface 121.

In other words, the sterilizing light source controller 191 controls the sterilizing light source 130 such that it is turned off when a user's finger contacts the fingerprint contact surface 121, and turned on when a user's finger does not contact the fingerprint contact surface 121 and the fingerprint contact surface 121 is exposed.

The sterilizing light source 150 is controlled by the sterilizing light source controller 191 such that it is turned off after a predetermined duration has passed since it was turned on, so that a proper and effective amount of sterilizing light may be irradiated onto the fingerprint contact surface 121

The on and off operation of the sterilizing light source 150 is controlled by the sterilizing light source controller 191 independently of the on and off operation of the light source 110. However, since the sterilizing light source 150 is controlled such that it is turned off when a user's finger accesses the fingerprint contact surface 121, interference does not occur between the light irradiated from the sterilizing light source 150 and the light irradiated from the light source 110 for fingerprint recognition.

Accordingly, the sterilizing light source 150 performs on and off operations during time intervals between many users' alternating random accesses to irradiate sterilizing light on and around the fingerprint contact surface 121 right after each access, performing sterilizing operations.

Figure 2:
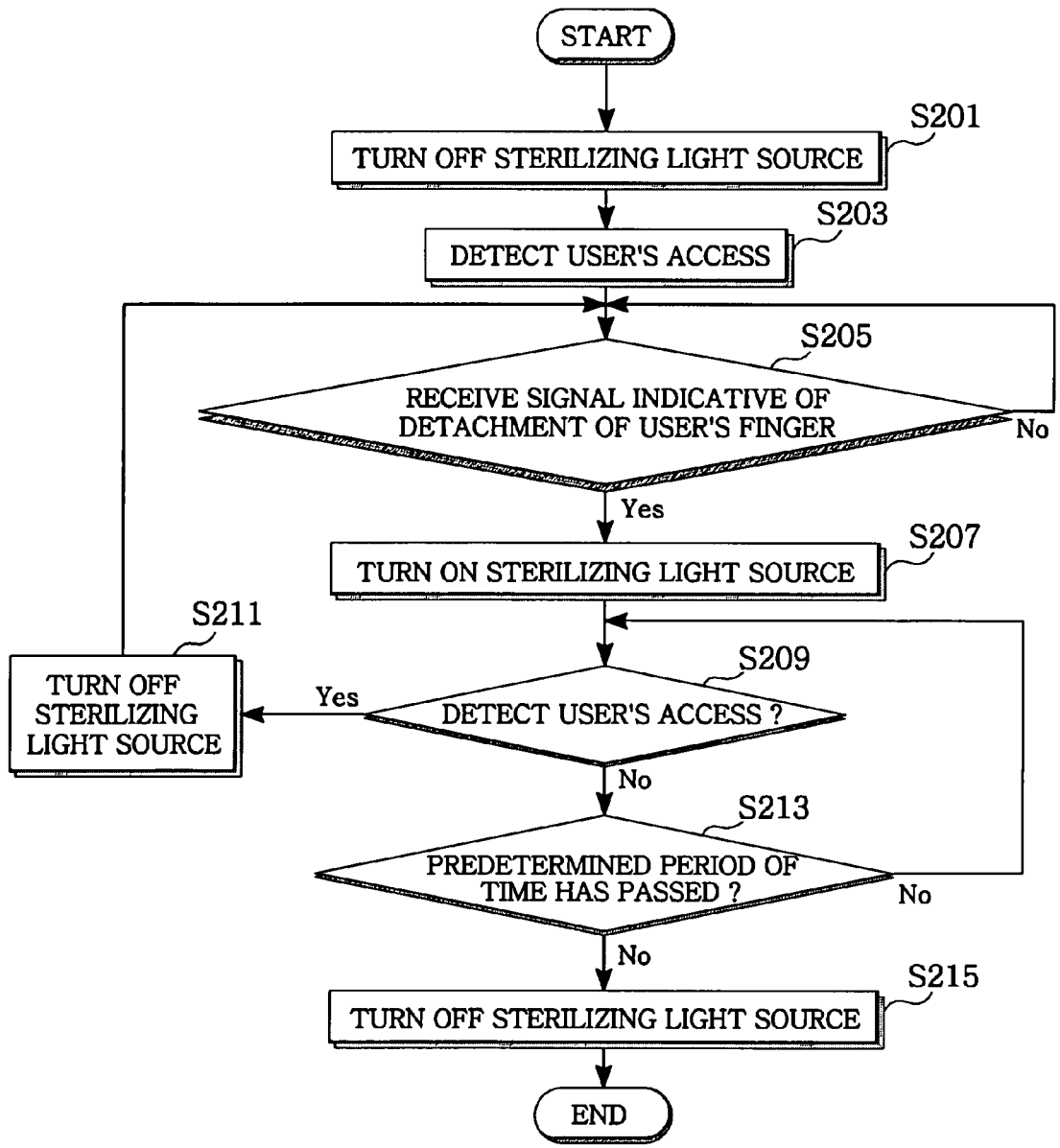
FIG. 2 is a flowchart illustrating a sterilizing operation of the optical type fingerprint recognition apparatus of FIG. 1.

A method for sterilizing a fingerprint recognition apparatus 200 according to an embodiment of the present invention will now be described with reference to FIG. 2.

A sterilizing light source controller 191 maintains a sterilizing light source 150 off if fingerprint recognition is not performed for a predetermined period of time (S201).

A sensor unit 160 detects whether a user's finger accesses a fingerprint contact surface 121 and, if so, transmits a detection signal to the sterilizing light source controller 191 (S203).

The sensor unit 160 also detects whether the user's finger is detached from the fingerprint contact surface 121 and, if so, transmits a signal indicative of the detachment of the user's finger to the sterilizing light source controller 191 (S205). Then, when the sterilizing light source controller 191 receives the signal indicative of the detachment of the user's finger, it turns on the sterilizing light source (S207). The sterilizing light source controller 191 may also turn on the sterilizing light source after a predetermined duration has passed since the user's finger was detached, to handle users' repeated accesses.

When the sterilizing light source controller 191 receives a detection signal indicative of a user's access to the fingerprint contact surface during the sterilizing (S209), the sterilizing light source controller 191 controls the sterilizing light source 150 to be turned off (S211).

And even if the sterilizing light source 150 were not turned off in S211, the sterilizing light source 150 is turned off when a predetermined duration has passed after the sterilizing light source 150 turned on (S213, S215).

An optical type fingerprint recognition apparatus using a prism can be sterilized by the above described algorithm. An optical type fingerprint recognition apparatus not using a prism, such as an optical type fingerprint recognition apparatus using a hologram, may also be sterilized by the same algorithm with the help of a sterilizing light source 150, a sensor unit 160, and a sterilizing light source controller 191.

In addition, if operations of S201 through S209 are repeated several times to recognize a plurality of users' fingerprints without performing any sterilizing operation for the predetermined duration of S211, the control unit 190 may force the sterilizing operation for the predetermined duration after having the output unit 170 output a guide message regarding 'interruption of a fingerprint recognition process and execution of a sterilizing process' through a predetermined voice or image.

Figure 3:
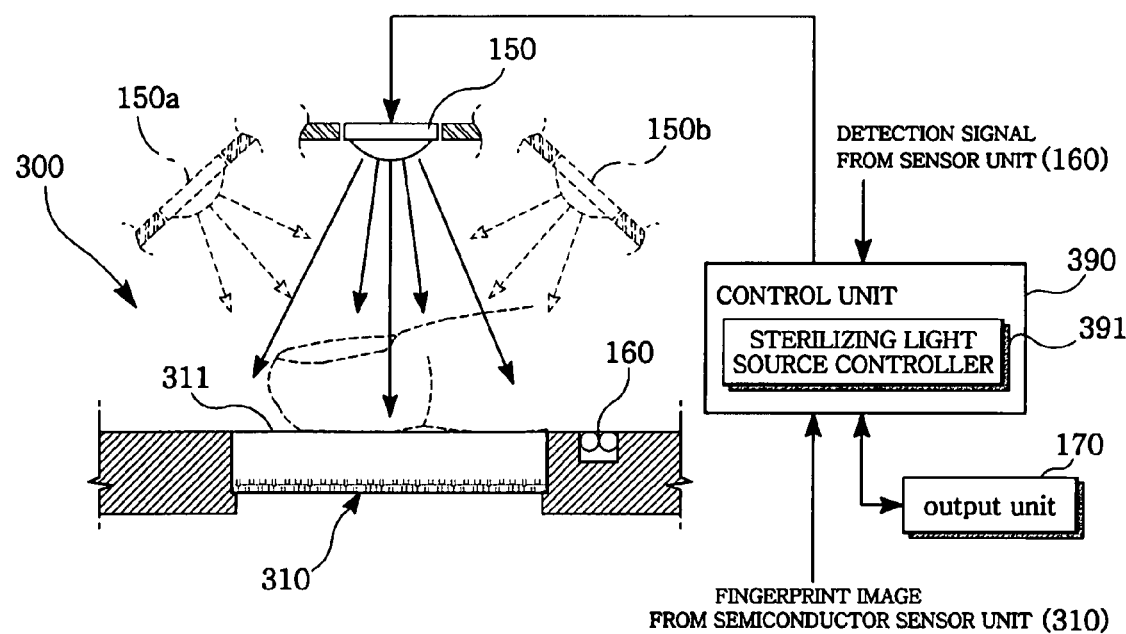
FIG. 3 is a schematic view illustrating main components of a non-optical type fingerprint recognition apparatus according to an embodiment of the present invention.

FIG. 3 is a schematic view illustrating main components of a non-optical type fingerprint recognition apparatus 300 including a sterilizing function according to an embodiment of the present invention.

The fingerprint recognition apparatus 300 includes a sterilizing light source 150 and a sensor unit 160 disposed around a semiconductor sensor 310, which is a fingerprint sensor unit and includes a sensor array, to irradiate sterilizing light onto a fingerprint contact surface 311 of the semiconductor sensor 310.

When a user's fingerprint contacts the fingerprint contact surface 311, the semiconductor sensor 310 of the fingerprint recognition apparatus 300 obtains a fingerprint image from the user's fingerprint and transmits it to a control unit 390. Then, the control unit 390 extracts minutiae data from the transmitted fingerprint image to perform an authentication process.

Description of a sterilizing light source 150 and a sensor unit 160 will be omitted because they performs substantially the same functions and operations as those in the previous embodiment. And a sterilizing light source controller 391 has the same function as the sterilizing light source controller 191 in FIG. 2.

However, the on and off operations of the sterilizing light source 150 may be unnecessary in a non-optical type fingerprint recognition apparatus 300 because the fingerprint recognition is not affected by the sterilizing light source 150.

Figure 4:
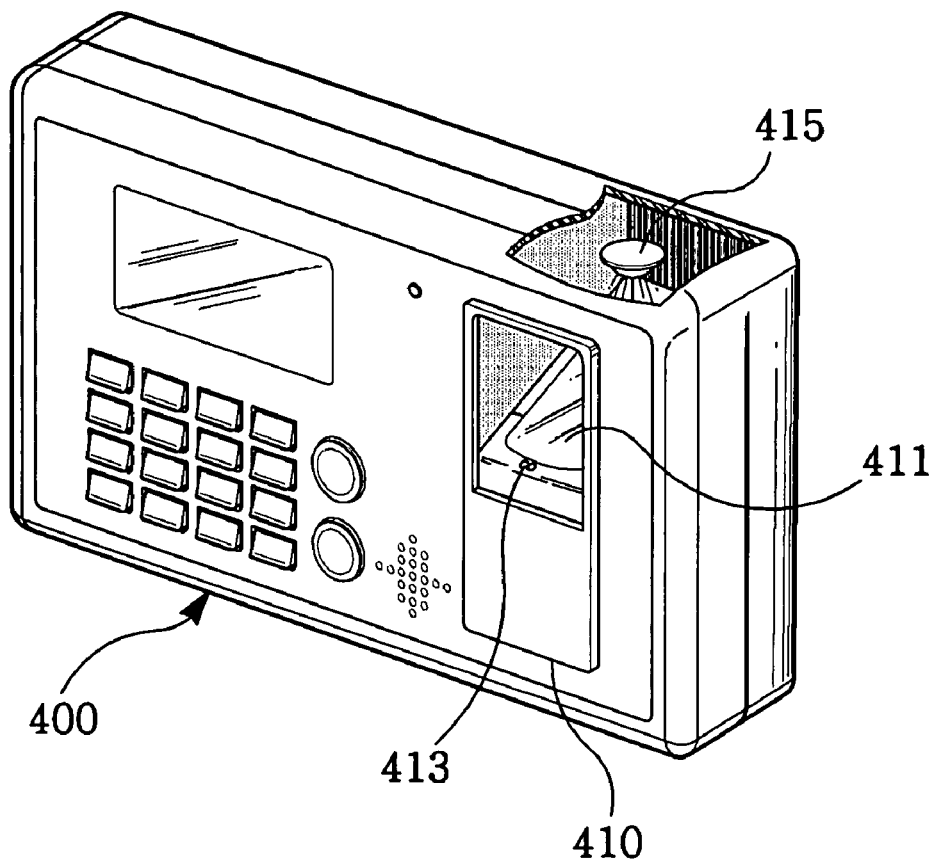
FIG. 4 is an exemplary perspective view illustrating a digital equipment including a fingerprint recognition apparatus according to an embodiment of the present invention.

As shown in FIG. 4, the fingerprint recognition apparatus 100 or 300 according to an embodiment of the present invention may be applied to a digital equipment 400 used by a plurality of users such as an access management equipment in order to add a sterilizing function thereto and improve hygienic conditions thereof. Referring to FIG. 4, a fingerprint recognition apparatus 410 is provided at one side of the digital equipment 400. The fingerprint recognition apparatus 410 includes a sterilizing light source 415 for irradiating sterilizing light onto a fingerprint contact surface 411 and a sensor unit 413 disposed in front of the fingerprint contact surface 411 to detect a user's access.

Figure 5:
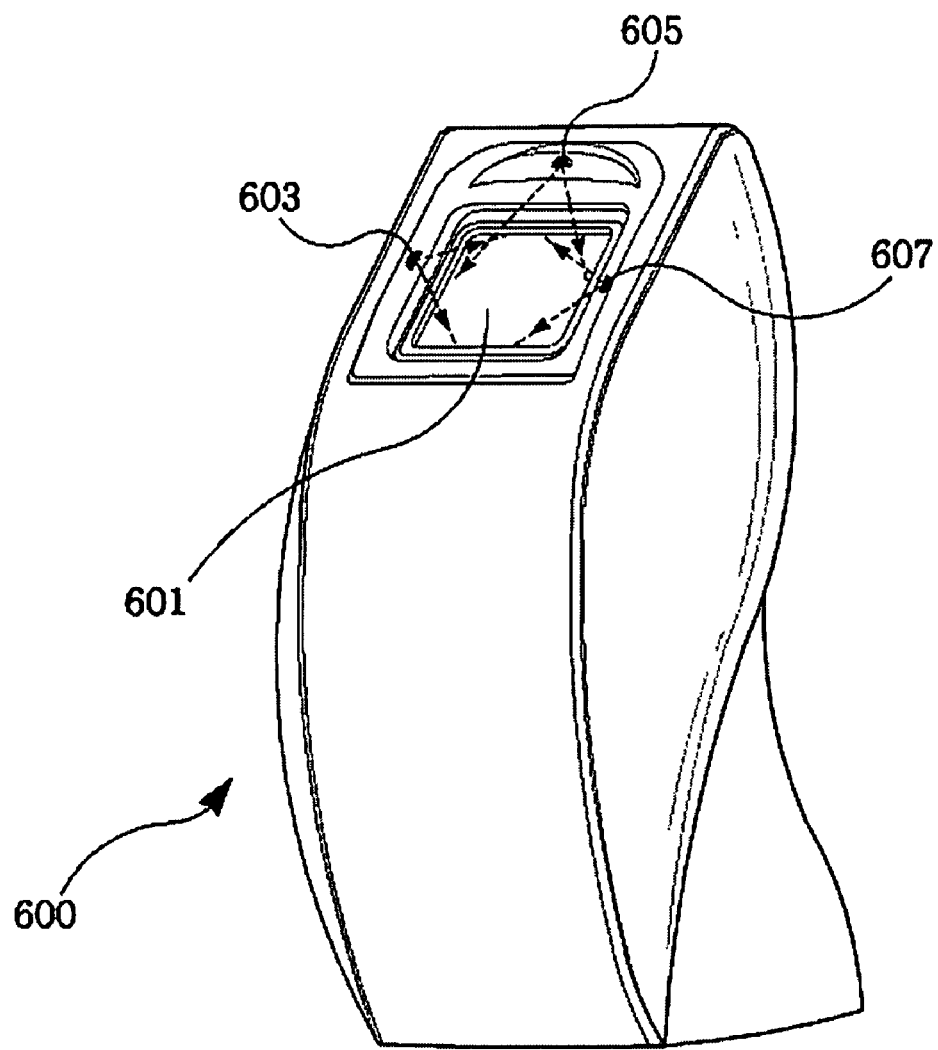
FIG. 5 is a perspective view illustrating a fingerprint recognition apparatus according to an embodiment of the present invention.

As shown in FIG. 5, a sterilizing light source 603, 605 or 607 may be disposed under the fingerprint contact surface 601 or at a lateral side of the fingerprint contact surface 601 when an additional housing is not provided above the fingerprint contact surface 601 of the fingerprint recognition apparatus 600.

As described above, the fingerprint recognition apparatus according to embodiments of the present invention sterilizes at all times a fingerprint contact surface which many and unspecified users contact their fingers on repeatedly. Accordingly, it is possible to prevent a route of bacterial infection and improve hygienic conditions.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. A fingerprint recognition apparatus comprising;
    a fingerprint sensor unit for obtaining a fingerprint image of a finger that contacts a fingerprint contact surface disposed on the fingerprint sensor unit;
    a control unit for performing a fingerprint recognition process on the basis of the fingerprint image obtained by the fingerprint sensor unit;
    a sterilizing light source for irradiating sterilizing light onto the fingerprint contact surface,
    a sensor unit disposed around the fingerprint contact surface to detect an exposure state of the fingerprint contact surface; and
    a sterilizing light source controller for controlling the sterilizing light source such that the sterilizing light source is selectively turned on/off depending on information detected by the sensor unit,
    wherein the sterilizing light source controller controls the sterilizing light source such that the sterilizing light source is turned on toward the fingerprint contact surface for a predetermined duration when it is determined, depending on the information detected by the sensor unit, that a user's finger is detached from the fingerprint contact surface after contacting the fingerprint contact surface, and wherein the sterilizing light source controller controls the sterilizing light source such that the sterilizing light source is turned off when it is determined, depending on the information detected by the sensor unit, that a user's finger accesses the fingerprint contact surface before the predetermined duration has passed since the sterilizing light source was turned on.

2. The fingerprint recognition apparatus according to claim 1, the apparatus further comprising an output unit for outputting a guide message requesting the user to stop contacting the fingerprint contact surface in response to a predetermined control signal, wherein the control unit transmits the predetermined control signal to the output unit when operations of determining that a user's finger accesses the fingerprint contact surface before the predetermined duration has passed since the sterilizing light source was turned on are repeated at least a predetermined number of times.

3. The fingerprint recognition apparatus according to claim 1, the apparatus further comprising an internal light source irradiating light for obtaining the fingerprint image on a rear side of the fingerprint contact surface, the rear side being an opposite side of a fingerprint-contacting side of the fingerprint contact surface, wherein the sterilizing light source is disposed around the internal light source to irradiate the sterilizing light on the rear side of the fingerprint contact surface.

4. The fingerprint recognition apparatus according to claim 1, wherein the sterilizing light source comprises a light emitting device that emits one of an infrared ray and an ultraviolet ray having sterilizing characteristics.

5. The fingerprint recognition apparatus according to claim 1, wherein the sterilizing light source is at least one of a point light source, an array type light source, a linear light source and a planar light source.

6. A method for sterilizing a fingerprint recognition apparatus, the method comprising:

detecting an access of a user's finger to a fingerprint contact surface of the fingerprint recognition apparatus by using a sensor unit;

turning on a sterilizing light source to irradiate sterilizing light on the fingerprint contact surface for a predetermined duration when it is determined, depending on information detected by the sensor unit, that the user's finger is detached from the fingerprint contact surface after contacting the fingerprint contact surface; and turning off the sterilizing light source when it is determined, depending on information detected by the sensor unit, that a user's finger accesses the fingerprint contact surface before the predetermined duration has passed since the sterilizing light source was turned on.

7. The method for sterilizing a fingerprint recognition apparatus according to claim 6, the method further comprising outputting a guide message requesting that the user discontinue contacting the fingerprint contact surface when a predetermined number of operating cycles of the turning on and the turning off are performed in succession.

* * * * *